(12) United States Patent
Cohen Addad et al.

(10) Patent No.: US 7,009,393 B2
(45) Date of Patent: Mar. 7, 2006

(54) NUCLEAR MAGNETIC RESONANCE METHOD OF DETECTING AND MONITORING THE FLOCCULATION KINETICS OF HEAVY FRACTIONS OF A COMPLEX FLUID

(75) Inventors: Jean-Pierre Cohen Addad, Grenoble (FR); Marc Fleury, La Celle Saint Cloud (FR)

(73) Assignee: Institut Francais du Petrole, Rueil Malmaison Cedex (FR)

( * ) Notice: Subject to any disclaimer, the term of this patent is extended or adjusted under 35 U.S.C. 154(b) by 52 days.

(21) Appl. No.: 10/501,524

(22) PCT Filed: Jan. 16, 2003

(86) PCT No.: PCT/FR03/00127

§ 371 (c)(1),
(2), (4) Date: Jul. 16, 2004

(87) PCT Pub. No.: WO03/060539

PCT Pub. Date: Jul. 24, 2003

(65) Prior Publication Data

US 2005/0083052 A1    Apr. 21, 2005

(30) Foreign Application Priority Data

Jan. 16, 2002 (FR) ................... 02 00466

(51) Int. Cl.
*G01V 3/00* (2006.01)
(52) U.S. Cl. ...................... 324/303; 324/306
(58) Field of Classification Search ............. 324/303, 324/306, 307, 309, 312, 314, 300
See application file for complete search history.

(56) References Cited

U.S. PATENT DOCUMENTS 5,387,865 A * 2/1995 Jerosch-Herold et al. ... 324/303

(Continued)

FOREIGN PATENT DOCUMENTS

EP          0 313 435          4/1989

(Continued)

OTHER PUBLICATIONS

A.N. Khryashchev et al. Determination of Layered-Packed Associates of Petroleum Asphaltenes by Means of Fourier 1H NMR Spectroscopy; 1991; pp. 455-460.

(Continued)

*Primary Examiner*—Louis Arana
(74) *Attorney, Agent, or Firm*—Antonelli, Terry, Stout and Kraus, LLP.

(57) ABSTRACT

The invention relates to a nuclear magnetic resonance method of detecting and monitoring the flocculation kinetics of high molecular weight fractions of a complex fluid. The inventive method applies the following to the fluid: a first static polarization magnetic field and, subsequently, at least a second oscillating pulsed magnetic field which generates a nuclear magnetic resonance for the nuclei considered and the acquisition of relaxation signals from the nuclei in the fluid. Moreover, the method detects, in the relaxation signals, a first part P1 which is representative of the relaxation of the flocculated fractions in the fluid and a second part P2 which is representative of the relaxation of the liquid fraction of the fluid; and determines the flocculation rate of the fractions by comparison with values $M_x(t=0)$ and $M_{x1}(t=0)$ which were extrapolated at the start of the acquisition times of the two parts. The invention is suitable, for example, for monitoring the flocculation kinetics of generally asphaltene polar fractions which are contained in the dissolved state and/or in the stable colloidal state in a liquid hydrocarbon fluid.

8 Claims, 4 Drawing Sheets

U.S. PATENT DOCUMENTS 5,397,987 A * 3/1995 Garritano ............... 324/307
5,530,350 A * 6/1996 Dechene et al. ............ 324/306

FOREIGN PATENT DOCUMENTS

EP          0 605 948 A1    7/1994
WO          WO 01/35067 A2  5/2001

OTHER PUBLICATIONS

J.-A. Ostlund et al.; Flocculation Behaviour of Asphaltenes in Solvent/Nonsolvent Systems; Journal of Colloid and Interface Science; 2002; pp. 150-158.

Menezes S M C et al: Determination of Parameters of Compare Tendencies of Wax Precipitation in Different Brazilian Oils; Oct. 19, 2000; pp. 1-8.

Ruffier-Meray et al. Use of Pulsed NMR Spectroscopy of Measure the Amount of Solid in Waxy Crudes ; Jul. 1998 ; pp. 531-535.

Norinaga, K. et al, "Measurement of self-diffusion coefficient of asphaltene in pyridine by pulsed field gradient spin-echo H NMR", Energy Fuels; Energy and Fuels Sep./Oct. 2001, vol. 15, No. 5, Sep. 2001, pp. 1317-1318, XP002240691.

* cited by examiner

NUCLEAR MAGNETIC RESONANCE METHOD OF DETECTING AND MONITORING THE FLOCCULATION KINETICS OF HEAVY FRACTIONS OF A COMPLEX FLUID

BACKGROUND OF THE INVENTION

1. Field of the Invention

The invention relates to a nuclear magnetic resonance method of detecting and monitoring the flocculation kinetics of high molecular weight fractions of a complex fluid.

2. Description of the Prior Art

Flocculation and deposition processes pose considerable problems in the petroleum industry. In particular for heavy oils, components of very high molar mass (asphaltenes, resins) are often the cause of such processes which may appear in porous media during production as well as during transportation. Flocculation is the formation of molecular aggregates of micronic size leading to sedimentation or deposition that can considerably modify the fluid flow, either by reduction of the section of flow or by viscosity increase. Furthermore, the intrinsic charge of some components (for example asphaltenes) generates a high tendency to cling to the charged surfaces.

The thermodynamic parameters which govern the flocculation processes are numerous (composition, pressure, temperature) and the complexity of the molecular structures involved make prediction and modelling very uncertain. Similarly, certain recovery methods ($CO_2$ injection, acidizing) may modify the fluid equilibria and bring about these processes. It is thus necessary to carry out measurements but the available techniques do not allow the first stages of the flocculation process to be observed and pose considerable implementation problems as regards pressure and temperature or in-situ problems in oil wells.

Many petroleum crudes, notably those referred to as asphaltene crudes, are liquid hydrocarbon fluids which contain more or less large amounts of heavy fractions in the dissolved state and/or in the stable colloidal state in the pressure and temperature conditions to which the fluids are subjected. When these pressure and/or temperature conditions vary, notably when the pressure decreases, the heavy fractions contained in these fluids tend to flocculate and to settle in the formation in the neighbourhood of wells, in wells and in production and transfer facilities intended for the fluids. Thus, when a hydrocarbon reservoir containing heavy fractions is developed, generally before the bubble point is reached, the stability of these fractions decreases. When the saturation threshold is reached, the heavy fractions flocculate and settle, which can cause clogging of the porous media and formation of plugs likely to severely damage production wells and surface installations.

For oil producers whose task is to extract and convey, through production wells and pipe networks, liquid hydrocarbon fluids of petroleum crudes containing heavy fractions, for example asphaltene crudes, from production fields, it is therefore important to have precise knowledge of the pressure thresholds below which the heavy fractions settle, so as to carry out production and transfer of the fluids under pressure and temperature conditions preventing deposition of the heavy fractions in installations or to provide a suitable treatment.

Various methods of determining the deposition threshold of heavy fractions, notably asphaltenes, contained in liquid hydrocarbon fluids of petroleum crudes are known. These methods are most often optical light transmission or diffusion methods, conductimetric methods or viscosimetric methods.

A method known as the "spot test" deposits a small quantity of a mixture on a filter paper and observes the spot that forms. The flocculation aggregates that form in a mixture diffuse less readily than the surrounding liquid. Thus, if the spot is not uniform, it is an indication that it contains flocculating particles.

The aforementioned methods use detection of the variation of a physical quantity, for example an absorption coefficient or absorbance of light rays in the visible range or in the infrared range, electrical conductivity or viscosity, which results from the change in the structure of the fluid following flocculation and deposition of heavy fractions.

A major drawback of such methods is that they are not very selective insofar as it is not always easy to relate the variation of the physical quantity measured to the flocculation and deposition of heavy fractions, and these methods are not always sensitive to the deposition of a small amount of such fractions. Some methods, such as absorbance measurement in the infrared range, are very sensitive but difficult to implement under reservoir conditions.

Furthermore, since these methods are often used in the laboratory, the question which has to be considered is the representativity of the samples on which the physical quantity measurements are carried out. In fact, for a sample to be representative of the sampled fluid, it is necessary to maintain this sample under the pressure and temperature conditions that prevail for the sampled fluid, for example reservoir fluid, throughout the sampling, sample transport and storage operations preceding the measurements.

French patent 2,818,753 filed by the assignee describes a method of determining the deposition threshold of heavy fractions contained, in the dissolved state and/or in the stable colloidal state, in a liquid hydrocarbon fluid. The invention provides a method of determining the deposition threshold of heavy fractions, notably asphaltenes, contained in the dissolved state and/or in the stable colloidal state in a liquid hydrocarbon fluid, using the formation of an increasingly high pressure drop linked with the flow, at an increasing flow rate, of a sample of the fluid through a capillary passage. The fluid sample being in the dissolved state and/or in the stable colloidal state, at the inlet of a capillary passage a pressure drop which is at least equal to the difference between the pressure of the fluid sample and the bubble-point pressure of said sample is generated between the inlet and the outlet. A significant shift in the variation as a function of time of $\Delta P$ (difference between the pressure of the fluid at the capillary inlet and the pressure at the outlet) and of a quantity D representative of the flow of liquid flowing through the capillary passage is detected, which allows to characterize the deposition threshold of the heavy fractions of the fluid.

Besides, it is well-known that NMR devices can be used notably to measure certain physical characteristics of fluid mixtures such as hydrocarbons, notably the viscosity or the gas/oil ratio (GOR). The viscosity of the mixture and its GOR coefficient are obtained from the NMR measurement of a diffusion coefficient D and from the measurement of the longitudinal $T_1$ or transverse $T_2$ relaxation time. Such an application is for example described in WO-0,142,817 or U.S. Pat. No. 5,696,448, or in the following document:

Prammer, M. G. et al., (2001);"the Downhole NMR Fluid Analyser"; SPWLA 42$^{nd}$ Annual Logging Symposium.

It can be noted that these measurements are generally performed in a time interval after excitation which is unsuited to detection and interpretation of flocculation phenomena.

It is also well-known to use NMR devices to detect and monitor a very different phenomenon which is the crystallization of particles in fluids.

SUMMARY OF THE INVENTION

The inventors have observed that NMR type methods applied to the detection of solid particles can also surprisingly apply to non-solid particles of high molecular weight under slow rotation which progressively aggregate, and are checked so that their flocculation rate can be determined by means of this type of method.

The application of the method according to the invention is notably to monitor the flocculation kinetics of generally asphaltene polar fractions which are contained in the dissolved state and/or in the stable colloidal state in a liquid hydrocarbon fluid.

The nuclear magnetic resonance method of detecting and monitoring the flocculation kinetics of non-solid high molecular weight aggregates of a complex fluid comprises applying to the fluid a first static polarization magnetic field, then at least a second oscillating pulsed magnetic field perpendicular to the first one, created by coils connected to an excitation generator for nuclear magnetic resonance of the nuclei being considered and acquisition of the relaxation signals of the nuclei in the fluid.

The method comprises detecting, regarding the relaxation signals, a first part representative of the relaxation of these aggregates in the fluid and a second part representative of the relaxation of the liquid fraction of the fluid, and determining the flocculation rate (Tf) of the aggregates by comparison of the values extrapolated at the start of the acquisition times of the first part and of the second part respectively.

The flocculation rate can be determined by means of the relation:

$$Tf=(M_x(t=0)-M_{x1}(t=0))/M_x(t=0)$$

where $M_x(t=0)$ and $M_{x1}(t=0)$ are the values extrapolated at the start of the acquisition times of the first part and of the second part respectively.

The flocculation threshold of the fluid can for example be obtained by modelling the relaxation signals actually obtained by means of a combination of exponential functions depending on an adjustment parameter and the threshold corresponding to a maximum value of said adjustment parameter is sought.

According to an implementation mode, the method comprises applying to the fluid a sequence of two 90° pulses referred to as pseudo-solid echoes in which a 180° magnetization focussing pulse is inserted, between two successive applications of the 90° pulses, with time intervals $\tau/2$ between the different pulses, and measuring the maximum amplitude of the relaxation signals in the neighbourhood of time $t=2\tau$ for different values of $\tau$ in the sequence.

The method affords many advantages. It allows continuous monitoring, useful for analysis of the flocculation as a function of the chemical composition and of the solvent. All of the volume is analyized. Unlike optical methods, even the non-transparent samples can beanalyized. Characterization of the kinetics is easy. It is also easy to evaluate the aggregate ratio, which can lead to an approximate estimation of the molecular weight.

BRIEF DESCRIPTION OF THE DRAWINGS

Other features and advantages of the method according to the invention will be clear from reading the description hereafter of non-limitative embodiment examples, with reference to the accompanying drawings wherein.

Figure 3:
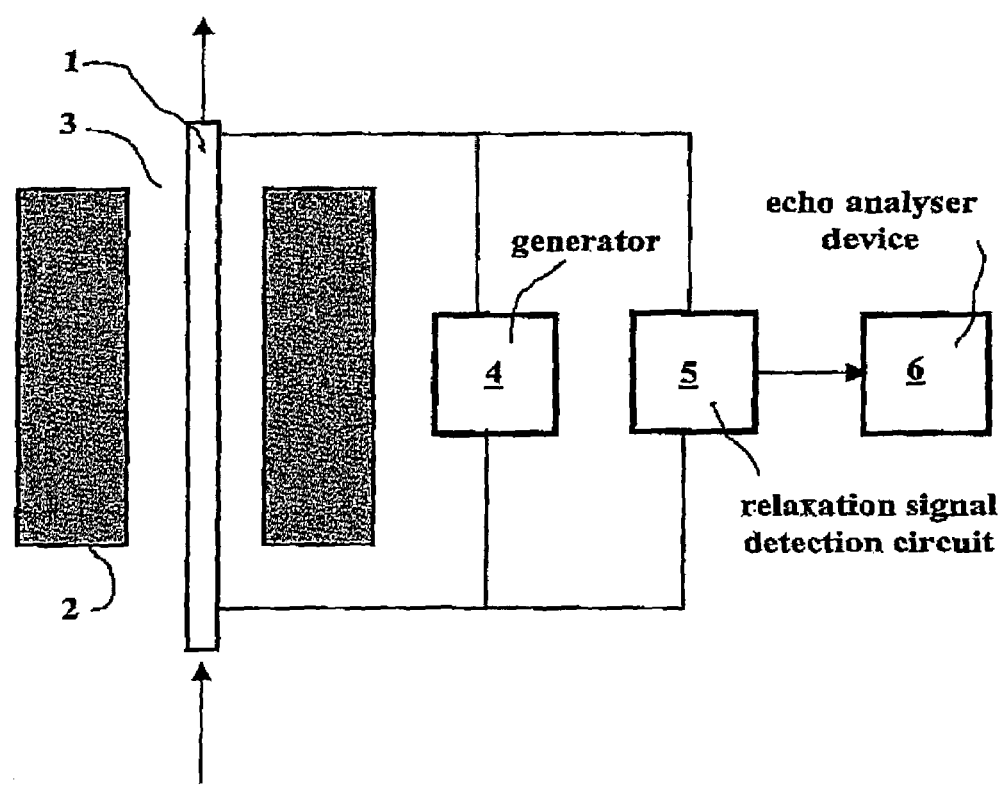

DETAILED DESCRIPTION OF THE INVENTION analysis technique essentially applies to an object to be tested a first static polarization magnetic field Bo intended to align the nuclei of the initially randomly oriented hydrogen protons, in the direction of the field, then a second oscillating pulsed magnetic field at the Larmor frequency, perpendicular to the first one, created by coils excited by a control signal to carry out a nuclear magnetic resonance experiment. When this pulsed field stops, the return of the nuclei to their initial state or relaxation generates electromagnetic signals (echoes) that are detected and analysed. The presence of such and such substance and some of its physical parameters are determined from the amplitude characteristics of these signals.

cases where the analysis concerns a fluid mixture, line 1 in which it circulates (or possibly the vessel that contains it) is conventionally passed (FIG. 3) first in the air gap of a permanent magnet 2 in which a static polarized field $B_0(z)$ prevails in a direction z, then in a coil 3 connected on the one hand to a generator 4 delivering on demand a current pulse at a frequency in the radio frequency range creating an oscillating pulsed transverse field $B_1(t)$ in a direction x perpendicular to direction z, and on the other hand to a relaxation signal detection circuit 5.

Within the scope of the method according to the invention, analysis of the relaxation of the transverse magnetization $M_x(t)$ of the protons of a liquid considered, observed at short times, is applied to detection of the flocculation, to determines the proportion of coarse structures formed in suspension in a liquid and to characterize the kinetics governing this formation process.

The procedure can be carried out conventionally using a sequence referred to as Hahn sequence or a sequence referred to as pseudo-solid echo sequence. After polarization by the static magnetic field $Bo(z)$ of the order of 0.5 T for example, a pulse field $B_1(t)$ having for example a tilt front and a receiver desaturation time below some microseconds is applied by means of coils 3. A sequence of at least two 90° pulses separated by a time interval $\tau$ is applied, with an inserted 180° pulse focusing the magnetization and thus being free from the diamagnetic heterogeneities of the material. The pulse application times are separated by time intervals $\tau/2$. The sequence can be schematized in time as follows:

(90°)x–$\tau/2$–(180°)y–$\tau/2$–(90°)x-echo acquisition.

By analyizing the echoes by means of a device 6, their maximum amplitude $M_x(t)$ in the vicinity of time $t=2\tau$ is determined for different values of $\tau$ in the above sequence.

Figure 2:
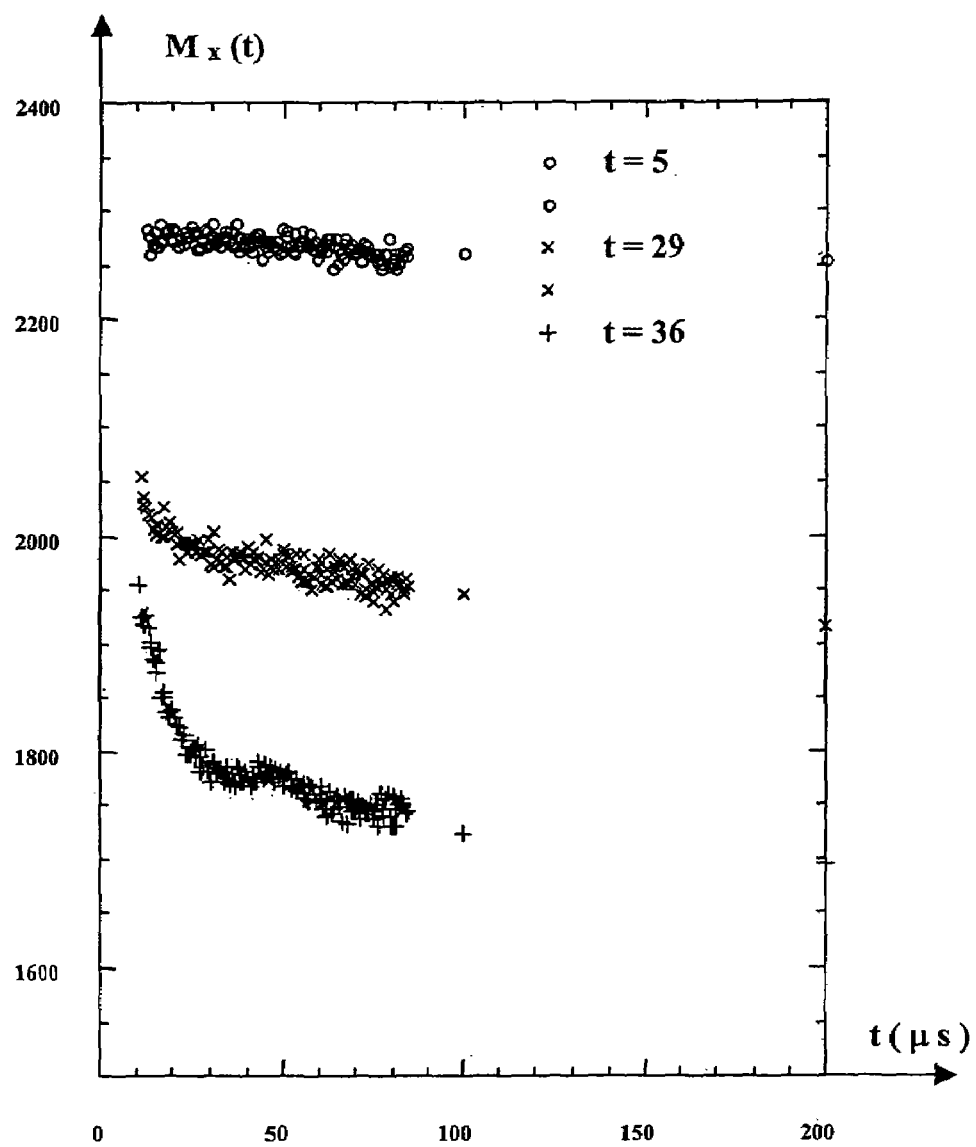
FIG. 2 shows the decrease curves of the transverse magnetization measured for an initially non-flocculated, then flocculated mixture, FIG. 3 diagrammatically shows a NMR type analysis device.

For a liquid in which certain fractions have flocculated, the relaxation signal has two clearly distinct parts corresponding to the appearance of the coarse structures in the liquid : a first part decreasing very rapidly within about twenty microseconds and whose size increases regularly with the formation of the flocculated structures, and a second part decreasing very slowly within several hundred milliseconds and corresponding to the liquid part of the fluid (FIG. 2). The flocculated structures produce fast decrease of the magnetization because they can be considered to be congealed (nearly solid). They are thus clearly distinguished from the magnetic properties of the surrounding liquid. Besides, the flocculated structures are also subjected to the Brownian movement generated by the thermal agitation of the liquid, but this random movement is too long to induce a magnetic relaxation process. This approach applies when the average size of the structures exceeds some nanometers.

The flocculated aggregate rate Tf can be obtained by extrapolating the signal of the liquid part $M_{x1}$ at the time $t=0$.

Figure 1:
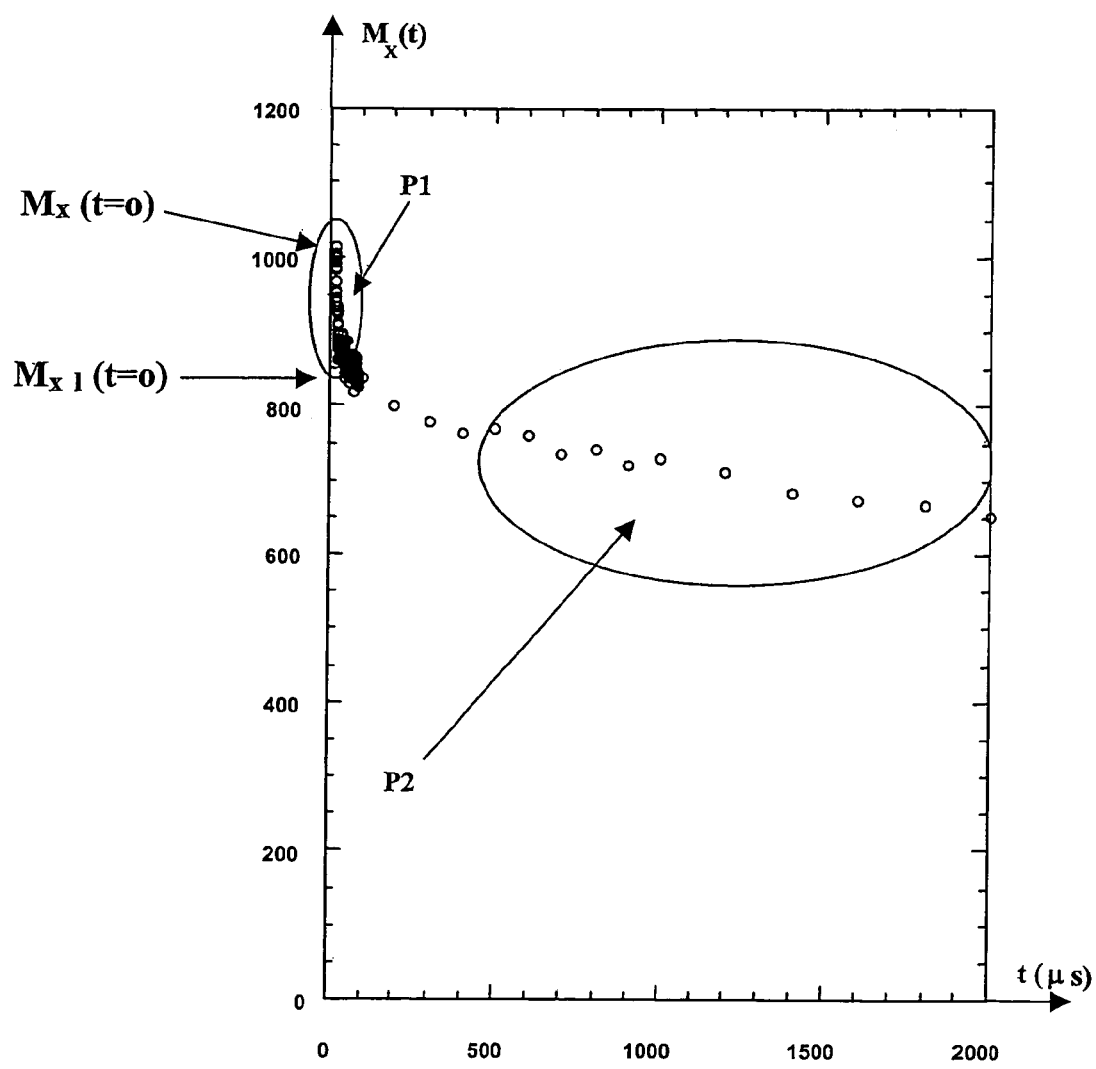
FIG. 1 shows the transverse magnetization decrease measured on a flocculated mixture.

A graphic method can be used when, as in the example of FIG. 1, the distribution of the points relative to the liquid part of the fluid analysed is substantially linear. It is also possible to seek for example a polynomial of sufficient degree or, if necessary, a sum of exponential functions modelling the distribution of the points of the liquid part, and to deduce therefrom the extrapolated value at the time $t=0$.

Rate Tf is obtained from this value $M_{x1}(t=0)$ and from the corresponding value of the first part of the distribution close to the start of the times, similarly extrapolated at the time $t=0$, i.e. $M_x(t=0)$. For example, Tf can be defined by the relation:

$$Tf=[M_x(t=0)-M_{x1}(t=0)]/M_x(t=0) \quad (1)$$

where $M_{x1}=M_x(t>tc)$, tc being the time separating the two decrease regions of $M_x(t)$. It is implicitly assumed that the total mass analysed does not change.

Detection of the first part of the relaxation distribution (FIG. 1) implies that the relaxation signals are acquired practically from the start of the times, that is within an interval greatly below 1 ms, which is not the case with the conventional methods using NMR analysis devices.

Observation of the flocculation kinetics as a function of time is illustrated in FIG. 2 for a viscous liquid (100 centipoise). At t=5 days, there is no flocculation because the signal shows no fast decrease. At t=29 days, certain flocculated structures appear and become more numerous at t=36 days. The acquisition time for a curve $M_x(t)$ being some minutes, faster kinetics can readily be observed.

The method application example below, which relates to asphaltene/toluene/heptane solutions, clearly shows a flocculation threshold detection mode.

Figure 4:
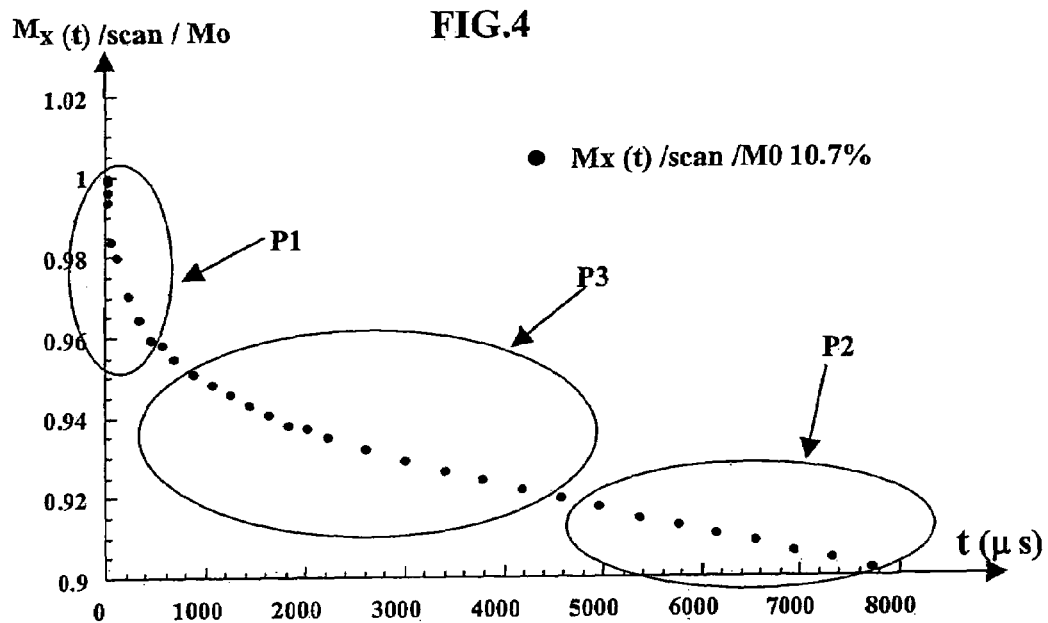
FIG. 4 shows the relaxation signal of an asphaltene/toluene/heptane solution.

It is well-known that, when the proportion of heptane increases, this type of solution flocculates. FIG. 4 shows an example of transverse magnetization signals (Mx(t)) obtained with these solutions. Parts P1 and P2 described above are connected by an intermediate part P3. In general, the signals are correctly described by a function which is a sum of exponentials. In the following function:

$$Mx(t)=\exp[-(t/\tau)^\alpha]+A\exp(-t/T_{2s}) \quad (2)$$

the second term $A\exp(-t/T_{2S})$ is characteristic of the relaxation time of the heptane/toluene mixture. Equation 2 is useful for separating the high molecular weight part characterized by very short relaxation times (order of magnitude $\tau$) from that of the heptane/toluene mixture (order of magnitude $T_{2S}$). The first term describes part P1 and intermediate part P3. For the mixture considered, the high molecular weight structures are visible before flocculation.

The value of A is obtained by determining the coefficients of relation 2 so that the modelled curve coincides with the curve of FIG. 4.

The aggregation rate of this mixture is calculated by means of the following relation:

$$Tf=(1-A)/A \quad (3)$$

This way of calculating Tf is equivalent to that obtained when applying relation 1. Monitoring of the evolution of coefficient A or, in an equivalent manner, of Tf, shows that the flocculation threshold corresponds to the maximum of this coefficient, in agreement with standard techniques.

Figure 5:
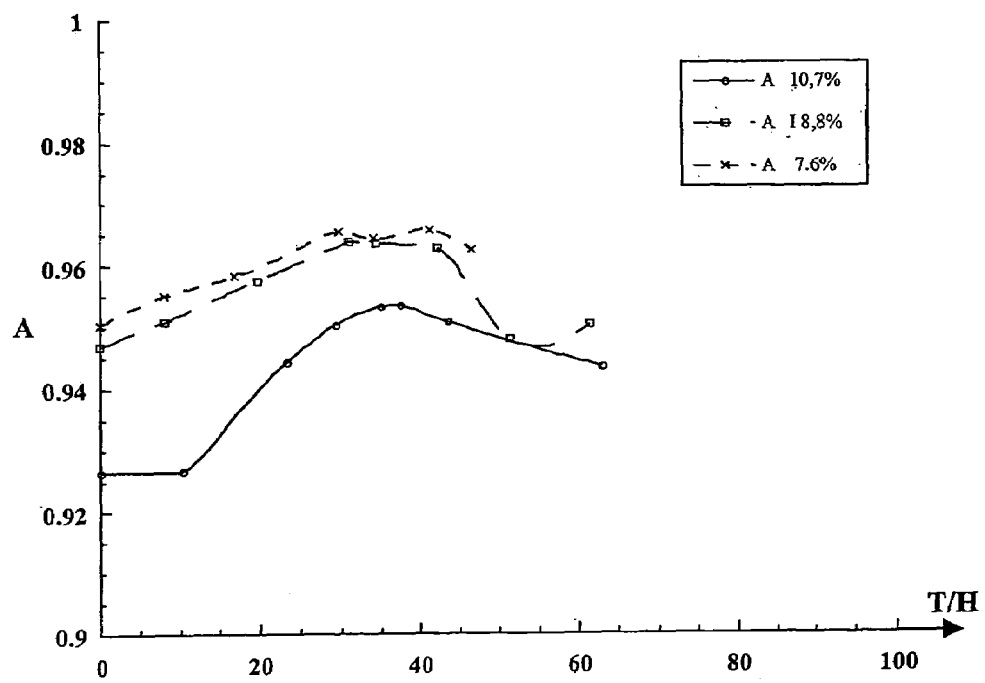
FIG. 5 shows the evolution of the coefficient A of a function modelling the relaxation signal of FIG. 4, which allows to locate the value of the flocculation threshold.

FIG. 5 shows the evolution of coefficient A as a function of the proportion T/H of toluene/heptane when the asphaltene concentration is 10.7, 8.8 and 7.6% respectively. It can be seen that the flocculation threshold at the heptane-toluene mass proportion 35 –65% shown by the arrow corresponds to the maximum of A.

The NMR measuring device used for implementing the method can be miniaturized in order to be installed in an oil well in combination with a formation-test tool of a well-known type in any other surface installation to monitor the flocculation phenomena. Whatever the analysis conditions, about 50 mg. substance are sufficient in practice.

The invention claimed is:

1. A nuclear magnetic resonance method of detecting and monitoring the flocculation kinetics of non-solid high molecular weight aggregates of a complex fluid comprising:
    applying to the fluid a first static polarization magnetic field, then at least a second oscillating pulsed magnetic field perpendicular to the first magnetic field, created by coils connected to an excitation generator for nuclear magnetic resonance of nuclei being considered and acquisition of relaxation signals of the nuclei in the fluid;
    detecting, for the relaxation signals, a first part representative of relaxation of the aggregates in the fluid and a second part representative of relaxation of a liquid fraction of the fluid; and
    determining a flocculation rate of the fraction by comparison of values $M_x(t=0)$ and $M_{x1}(t=0)$ extrapolated at a start of acquisition times of the first part and of the second part respectively.

2. A method as claimed in claim 1, wherein:
    the flocculation rate is determined by the relation:
    $$Tf=(M_x(t=0)-M_{x1}(t=0))/M_x(t=0).$$

3. A method as claimed in claim 2, comprising:
    applying to the fluid a sequence of two 90° pulses in which a 180° magnetization focussing pulse is inserted, between two successive applications of the 90° pulses, with time intervals $\tau/2$ between the application of the 90° pluse, and measuring a maximum amplitude of the relaxation signals in a vicinity of time $t=2\tau$ for different values of $\tau$ in the sequence of two 90° pulses.

4. A method as claimed in claim 2, wherein:
    a flocculation threshold of the fluid is obtained by modelling the relaxation signals actually obtained by means of a combination of exponential functions depending on an adjustment parameter and a threshold corresponding to a maximum value of the adjustment parameter.

5. A method as claimed in claim 4, comprising:
applying to the fluid a sequence of two 90° pulses in which a 180° magnetization focussing pulse is inserted, between two successive applications of the 90° pulses, with time intervals $\tau/2$ between the application of the 90° pulses, and measuring a maximum amplitude of the relaxation signals in a vicinity of time $t=2\tau$ for different values of $\tau$ in the sequence of two 90° pulses.

6. A method as claimed in claim 1, wherein:
a flocculation threshold of the fluid is obtained by modelling the relaxation signals actually obtained by means of a combination of exponential functions depending on an adjustment parameter and a threshold corresponding to a maximum value of the adjustment parameter.

7. A method as claimed in claim 6, comprising:
applying to the fluid a sequence of two 90° pulses in which a 180° magnetization focussing pulse is inserted, between two successive applications of the 90° pulses, with time intervals $\tau/2$ between the application of the 90° pulses, and measuring a maximum amplitude of the relaxation signals in a vicinity of time $t=2\tau$ for different values of $\tau$ in the sequence of two 90° pluses.

8. A method as claimed in claim 1, comprising:
applying to the fluid a sequence of two 90° pulses in which a 180° magnetization focussing pulse is inserted, between two successive applications of the 90° pulses, with time intervals $\tau/2$ between the application of the 90° pulses, and measuring a maximum amplitude of the relaxation signals in a vicinity of time $t=2\tau$ for different values of $\tau$ in the sequence of two 90° pulses.

* * * * *